United States Patent
Wilson et al.

(10) Patent No.: US 11,771,435 B2
(45) Date of Patent: Oct. 3, 2023

(54) EXPANDABLE IMPLANT AND IMPLANT SYSTEM

(71) Applicants: LAWRENCE LIVERMORE NATIONAL SECURITY, LLC, Livermore, CA (US); THE TEXAS A&M UNIVERSITY SYSTEM, College Station, TX (US)

(72) Inventors: Thomas S. Wilson, San Leandro, CA (US); Ward Small, IV, Livermore, CA (US); William J. Benett, Livermore, CA (US); Jason M. Ortega, Pacifica, CA (US); Duncan J. Maitland, College Station, TX (US); Jonathan Hartman, Sacramento, CA (US)

(73) Assignees: Lawrence Livermore National Security, LLC, Livermore, CA (US); The Texas A&M University System, College Station, TX (US)

(*) Notice: Subject to any disclaimer, the term of this patent is extended or adjusted under 35 U.S.C. 154(b) by 329 days.

(21) Appl. No.: 17/155,493

(22) Filed: Jan. 22, 2021

(65) Prior Publication Data

US 2021/0137527 A1    May 13, 2021

Related U.S. Application Data

(63) Continuation of application No. 15/984,003, filed on May 18, 2018, now Pat. No. 10,898,199, which is a
(Continued)

(51) Int. Cl.
*A61B 17/12* (2006.01)
*A61B 17/00* (2006.01)
(Continued)

(52) U.S. Cl.
CPC .... *A61B 17/12113* (2013.01); *A61B 17/1214* (2013.01); *A61B 17/1215* (2013.01);
(Continued)

(58) Field of Classification Search
CPC .......... A61B 17/12113; A61B 17/1214; A61B 17/12145; A61B 17/1215;
(Continued)

(56) References Cited

U.S. PATENT DOCUMENTS 4,706,671 A    11/1987   Weinrib
4,994,069 A    2/1991    Ritchart et al.
(Continued)

FOREIGN PATENT DOCUMENTS

EP    2651462        7/2015
WO    2004016205 A2  2/2004
(Continued)

OTHER PUBLICATIONS

Canadian Intellectual Property Office, Examination Search Report dated Feb. 2, 2018 in Canadian Patent Application No. 2,821,151.
(Continued)

*Primary Examiner* — Ashley L Fishback
(74) *Attorney, Agent, or Firm* — TROP, PRUNER & HU, P.C.

(57) ABSTRACT

An embodiment of the invention includes an expandable implant to endovascularly embolize an anatomical void or malformation, such as an aneurysm. An embodiment is comprised of a chain or linked sequence of expandable polymer foam elements. Another embodiment includes an elongated length of expandable polymer foam coupled to a backbone. Another embodiment includes a system for endovascular delivery of an expandable implant (e.g., shape memory polymer) to embolize an aneurysm. The system may include a microcatheter, a lumen-reducing collar
(Continued)

coupled to the distal tip of the microcatheter, a flexible pushing element detachably coupled to an expandable implant, and a flexible tubular sheath inside of which the compressed implant and pushing element are pre-loaded. Other embodiments are described herein.

16 Claims, 15 Drawing Sheets

Related U.S. Application Data continuation of application No. 13/325,906, filed on Dec. 14, 2011, now Pat. No. 10,010,327.

(60) Provisional application No. 61/423,926, filed on Dec. 16, 2010, provisional application No. 61/423,920, filed on Dec. 16, 2010.

(51) Int. Cl.
*A61M 25/06* (2006.01)
*A61M 25/00* (2006.01)

(52) U.S. Cl.
CPC .. *A61B 17/12145* (2013.01); *A61B 17/12181* (2013.01); *A61B 17/12163* (2013.01); *A61B 2017/00871* (2013.01); *A61B 2017/12054* (2013.01); *A61M 25/0668* (2013.01); *A61M 2025/0042* (2013.01)

(58) Field of Classification Search
CPC ........ A61B 17/12181; A61B 17/12163; A61B 2017/00871; A61B 2017/12054; A61M 25/0668; A61M 2025/0042
See application file for complete search history.

(56) References Cited

U.S. PATENT DOCUMENTS

| | | | |
|---|---|---|---|
| 5,045,601 A | 9/1991 | Capelli et al. |
| 5,049,591 A | 9/1991 | Hayashi et al. |
| 5,354,295 A | 10/1994 | Guglielmi et al. |
| 5,418,261 A | 5/1995 | Helsemans et al. |
| 5,522,836 A | 6/1996 | Palermo |
| 5,690,671 A | 11/1997 | McGurk et al. |
| 5,846,247 A | 12/1998 | Unsworth et al. |
| 6,086,599 A | 7/2000 | Lee et al. |
| 6,102,917 A | 8/2000 | Maitland et al. |
| 6,156,842 A | 12/2000 | Hoenig et al. |
| 6,238,403 B1 | 5/2001 | Greene, Jr. et al. |
| 6,458,127 B1 | 10/2002 | Truckai et al. |
| 6,551,340 B1 | 4/2003 | Konya et al. |
| 6,583,194 B2 | 6/2003 | Sendijarevic |
| 6,616,617 B1 | 9/2003 | Ferrera et al. |
| 7,308,738 B2 | 12/2007 | Barvosa-Carter et al. |
| 7,386,203 B2 | 6/2008 | Maitland et al. |
| 7,422,714 B1 | 9/2008 | Hood et al. |
| 7,611,524 B1 | 11/2009 | Maitland et al. |
| 7,744,604 B2 | 6/2010 | Maitland et al. |
| 7,828,790 B2 | 11/2010 | Griffin |
| 8,343,167 B2 | 1/2013 | Henson |
| 8,449,592 B2 | 5/2013 | Wilson et al. |
| 9,018,273 B2 | 4/2015 | Ito et al. |
| 9,051,411 B2 | 6/2015 | Wilson et al. |
| 2002/0010481 A1 | 6/2002 | Jayaraman |
| 2002/0142119 A1 | 10/2002 | Seward et al. |
| 2003/0028209 A1 | 2/2003 | Teoh et al. |
| 2003/0236533 A1 | 12/2003 | Wilson et al. |
| 2004/0030062 A1 | 2/2004 | Mather et al. |
| 2005/0021074 A1 | 1/2005 | Elliott |
| 2005/0038460 A1 | 2/2005 | Jayaraman |
| 2005/0043755 A1 | 2/2005 | Wilson et al. |
| 2005/0075405 A1 | 4/2005 | Wilson et al. |
| 2005/0085693 A1 | 4/2005 | Belson et al. |
| 2005/0165480 A1 | 7/2005 | Jordan et al. |
| 2005/0192621 A1 | 9/2005 | Wallace et al. |
| 2005/0228417 A1 | 10/2005 | Teitelbaum et al. |
| 2005/0267570 A1 | 12/2005 | Shadduck |
| 2005/0274454 A1 | 12/2005 | Extrand |
| 2005/0274455 A1 | 12/2005 | Extrand |
| 2006/0009785 A1 | 1/2006 | Maitland et al. |
| 2007/0016233 A1 | 1/2007 | Ferrera et al. |
| 2007/0104752 A1 | 5/2007 | Lee et al. |
| 2007/0135907 A1 | 6/2007 | Wilson et al. |
| 2008/0019657 A1 | 1/2008 | Maitland et al. |
| 2008/0051829 A1 | 2/2008 | Eidenschink et al. |
| 2008/0109057 A1 | 5/2008 | Calabria et al. |
| 2008/0114454 A1 | 5/2008 | Peterman et al. |
| 2008/0269745 A1 | 10/2008 | Justin |
| 2009/0054918 A1 | 2/2009 | Henson |
| 2009/0093674 A1 | 4/2009 | Adams |
| 2009/0130391 A1 | 5/2009 | Taya |
| 2009/0248141 A1 | 10/2009 | Shandas et al. |
| 2009/0264835 A1 | 11/2009 | Schuermann |
| 2009/0280330 A1 | 11/2009 | Xie et al. |
| 2011/0015613 A1 | 1/2011 | Anzai |
| 2012/0158034 A1 | 6/2012 | Wilson et al. |
| 2013/0317541 A1 | 11/2013 | Singhal et al. |
| 2014/0277057 A1 | 9/2014 | Ortega et al. |

FOREIGN PATENT DOCUMENTS

| | | |
|---|---|---|
| WO | 2009013752 A2 | 1/2009 |
| WO | WO2012083051 | 6/2012 |

OTHER PUBLICATIONS

Xie, "Recent advances in polymer shape memory," Polymer, Aug. 10, 2011, pp. 4985-5000, vol. 52, Elsevier Ltd.
Ayranci et al., "Shape Memory Effect of a Thermoset Polymer and its Fiber Reinforced Composites," 18th International Conference on Composite Polymers, pp. 1-5.
Behl et al., "Shape-memory polymers," Materials Today, Apr. 2007, vol. 10, No. 4, pp. 20-28, Elsevier Ltd.
European Patent Office, Extended European Search Report dated Jun. 15, 2015 for European Patent Application No. 11848981.4.
European Patent Office, Communication pursuant to Article 94(3) EPC dated Feb. 27, 2017 for European Patent Application No. 11848981.4.
The International Searching Authority, Written Opinion of the International Searching Authority and the International Search Report dated Dec. 26, 2012 in International Application No. PCT/US2011/065220, nine pages.
Reddy et al., "Bioinspired Surfaces with Switchable Adhesion," Advanced Materials, 2007, vol. 19, pp. 3833-3837, Wiley-VCH Verlag GmbH & Co., KGaA, Weinheim.
Canadian Intellectual Property Office, Office Action dated Apr. 14, 2020, in Canadian Patent Application No. 2,821,151, 3 pages total.
Canadian Patent Office, Office Action dated Nov. 7, 2018 in Canadian patent application No. 2,821,151, 3 pages total.
Canadian Patent Office, Office Action dated Jul. 24, 2019 in Canadian patent application No. 2,821,151, 3 pages total.
European Patent Office, Extended European Search Report dated Dec. 6, 2021 in European Patent Application No. 20210827.0 (11 pages).

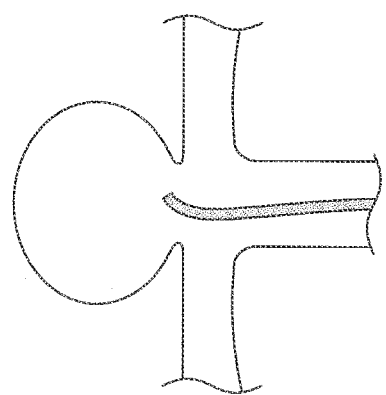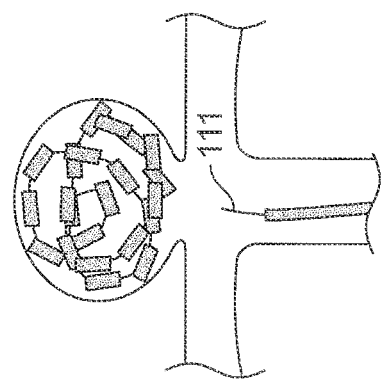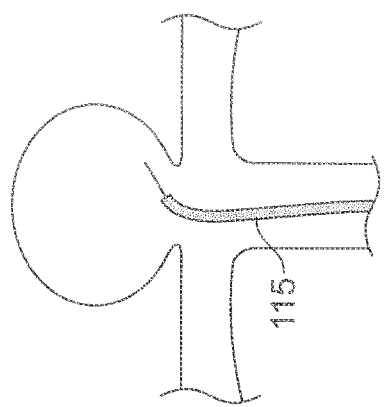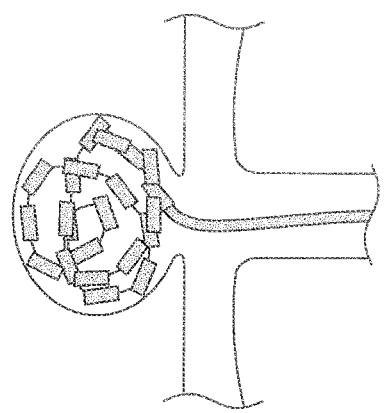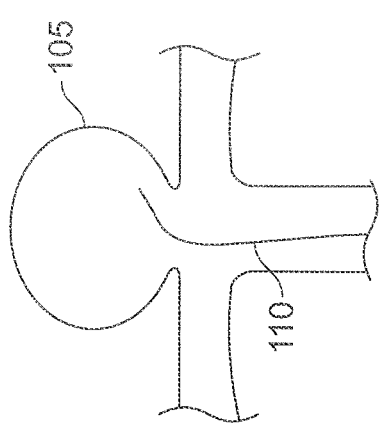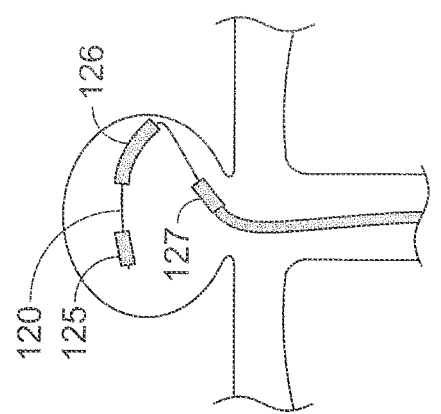

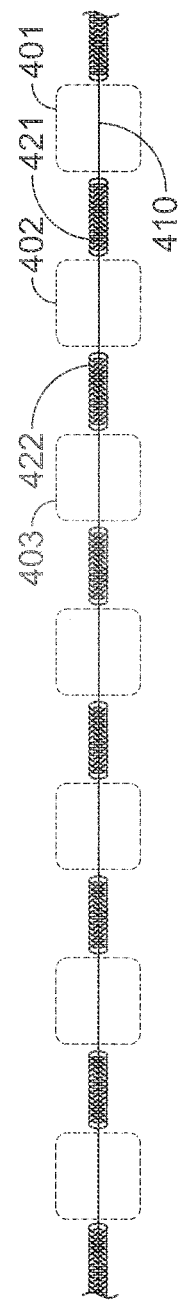
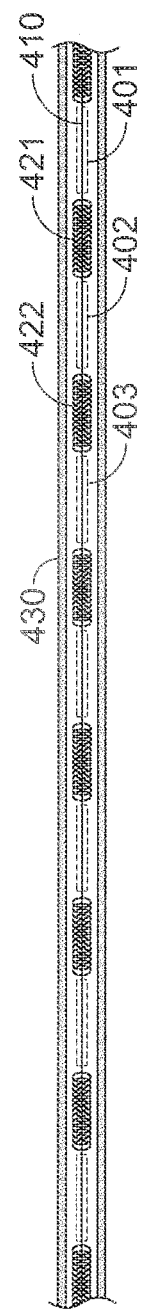
Fig. 4A
Fig. 4B

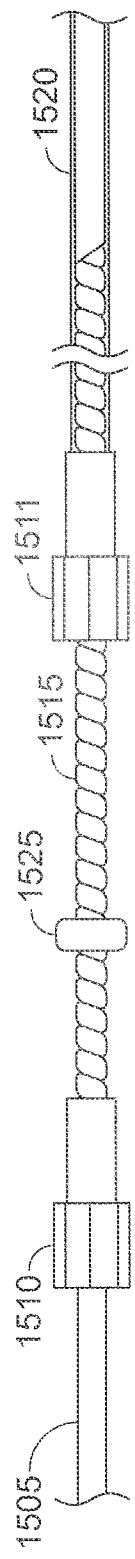
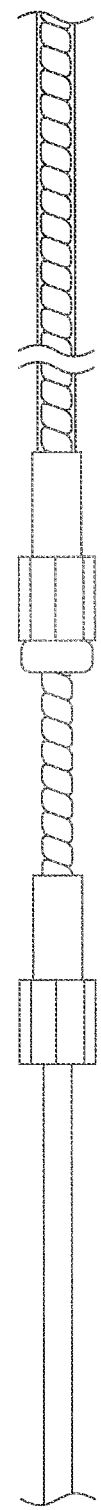
Fig. 15A
Fig. 15B

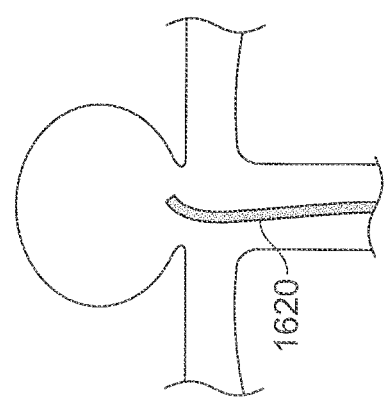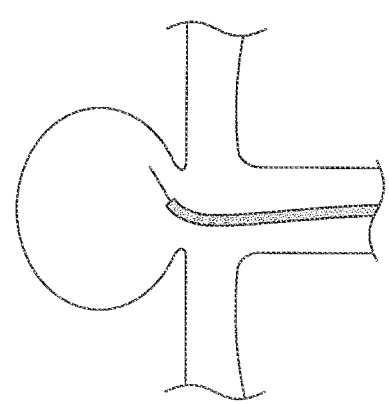
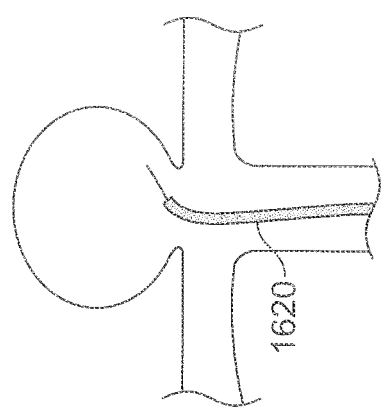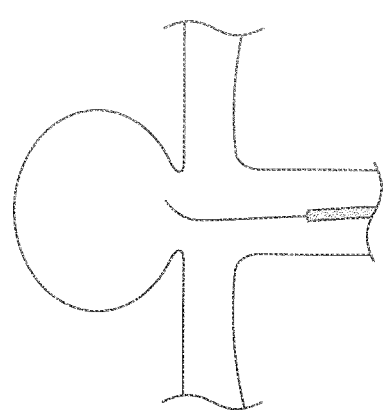
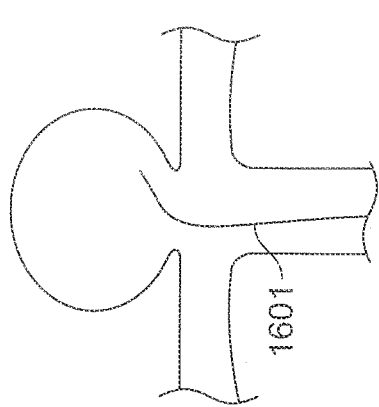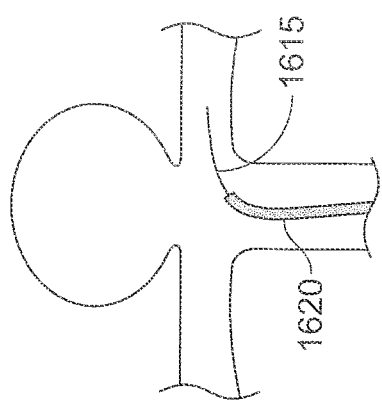

EXPANDABLE IMPLANT AND IMPLANT SYSTEM

CROSS-REFERENCE TO RELATED APPLICATION(S)

This application is a continuation of U.S. patent application Ser. No. 15/984,003, filed May 18, 2018, which is a continuation of U.S. patent application Ser. No. 13/325,906, filed Dec. 14, 2011, now U.S. Pat. No. 10,010,327, issued Jul. 3, 2018, which claims priority to both U.S. Provisional Patent Application No. 61/423,920, filed Dec. 16, 2010 and entitled "Apparatus for Endovascular Delivery of an Expandable Aneurysm Implant", and U.S. Provisional Patent Application No. 61/423,926 filed Dec. 16, 2010 and entitled "Expandable Aneurysm Implant". The content of each of the above applications is hereby incorporated by reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

Various embodiments of the invention concern the treatment of anatomical malformations. Some embodiments concern delivery systems for implants. Some embodiments concern expandable embolic agents. Some embodiments concern endovascular embolization of aneurysms using an expandable embolic agent.

BACKGROUND

Cerebral aneurysms may develop when a weakened area of a blood vessel (e.g., a blood vessel in or around the brain) bulges outward. If not treated, aneurysms can rupture resulting in hemorrhagic stroke, a major cause of mortality and long-term disability. Taking cerebral aneurysms for example, there are several modalities used to treat cerebral aneurysms including: (1) traditional surgical clipping, and (2) endovascular embolization. Surgical clipping is a traumatic procedure that involves craniotomy, retraction of the brain to expose the aneurysm, and placement of a metal clip across the aneurysm neck. Endovascular embolization is a minimally invasive technique in which embolic agents are delivered into the aneurysm via a catheter, under fluoroscopic (x-ray) guidance, to occlude the aneurysm and promote healing.

Regarding endovascular embolization, the Gugliemi Detachable Coil (GDC) allows a surgeon to deploy a helical platinum coil into the aneurysm. Once in proper position, the coil is detached from the delivery apparatus and released into the aneurysm. Multiple coils may be required to effectively fill the aneurysm and induce clotting and eventual sealing of the aneurysm from the parent vessel. Such coils are subject to problematic issues with recanalization and related insufficient healing.

Though not as prevalent as embolic coils, liquid embolic agents that solidify inside the aneurysm are also available for clinical use in rare cases. However, such agents can be difficult to precisely administer at specific sites.

BRIEF DESCRIPTION OF THE DRAWINGS

Features and advantages of embodiments of the present invention will become apparent from the appended claims, the following detailed description of one or more example embodiments, and the corresponding figures, in which:

FIGS. 1A-F include an embodiment for embolization of an aneurysm with an expandable apparatus delivered endovascularly.

FIGS. 4A-B include an embodiment with spacers located between expandable elements.

FIGS. 15A-B include an embodiment having a stop collar.

FIGS. 16A-I include an embodiment for a method of repositioning a misplaced embolization system.

DETAILED DESCRIPTION

Figure 2A:
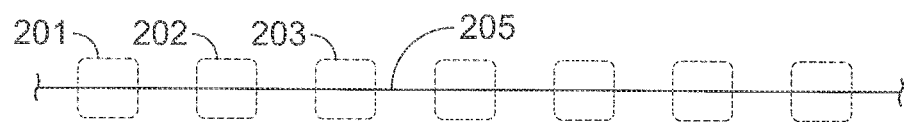
FIGS. 2A, 2B, 2C-1, 2C-2, D-F include embodiments of shape memory polymer (SMP) elements, backbones, and monolithic SMPs covering long portions of backbones.

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

An embodiment of the invention includes an expandable implant to endovascularly embolize (fill) an anatomical void or malformation, such as an aneurysm. An embodiment is comprised of a chain or linked sequence of expandable polymer foam elements. Another embodiment includes an elongated length of expandable polymer foam coupled to a backbone.

The expandable polymer foam may comprise a shape memory polymer (SMP) foam in some embodiments. SMP foam is capable of being compressed and retaining its stable compressed shape (i.e., "secondary" state or configuration). The expandable foam element(s) may be compressed radially and/or extended/stretched axially for endovascular delivery through a microcatheter. The SMP may subsequently return to its stable predetermined primary expanded form (i.e., "primary" state or configuration) when activated. Activation may include exposing the SMP to an appropriate stimulus (e.g., heat, electricity, light, electromagnetic energy, and the like). This transformation ability may be based, at least in part, on the polymer morphology of the SMP. In an embodiment, the morphology comprises a shape-fixing matrix phase (amorphous or semi-crystalline polymer) and a shape-memorizing dispersed phase (physical or chemical crosslinks). The primary shape may be programmed into the material during the SMPs original melt processing or curing process. The temporary secondary shape may be obtained by deforming the SMP while heating the SMP above the characteristic thermal transition temperature (Tt) and then cooling the SMP to fix the shape. In an embodiment, Tt may be the glass transition temperature (Tg) or melting temperature (Tm) depending on the polymer system. The expanded SMP foam may serve as a localized scaffold for blood clot formation, which fosters the healing process of an aneurysm.

Figure 2B:
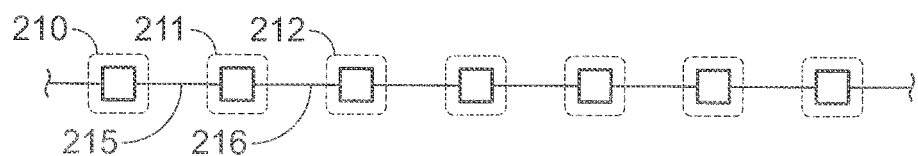
Figures 1, 2C:
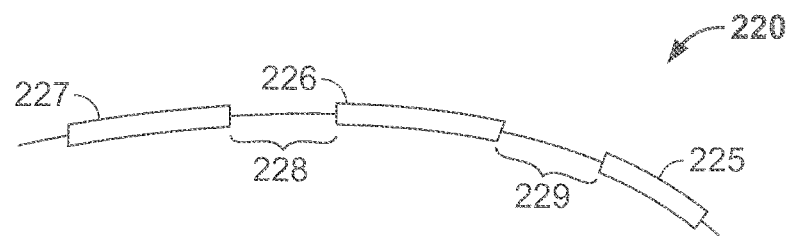

FIG. 1 includes an embodiment of the invention for embolization of an aneurysm with an expandable apparatus delivered endovascularly. In FIG. 1(a) guide wire 110 is advanced into aneurysm 105. In FIG. 1(b) microcatheter 115 is advanced along guide wire 110 into aneurysm 105. In FIG. 1(c) guide wire is withdrawn and no longer showing, leaving catheter 115 located in or near aneurysm 105. In FIG. 1(d) the expandable implant, comprising backbone 120 and SMP elements 125, 126, 127, is delivered from catheter 115 into aneurysm 105. FIG. 1(e) shows additional length of backbone 120 and additional SMP elements deployed within aneurysm 105. In FIG. 1(f) backbone 120 is detached from guide wire 111. After FIG. 1(f) catheter 115 and guide wire 111 are withdrawn from the patient.

As used herein, "guide wire" is a general term that connotes a wire or rod used to guide itself or other items through vasculature. Guide wire 111 may be thought of as a pusher rod that couples to backbone 120 to guide the backbone and SMP elements through catheter 115 and into aneurysm 105.

Figures 2, 2C:
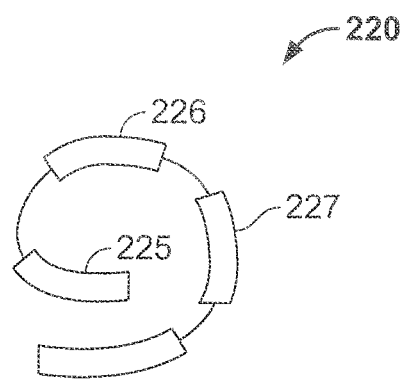

FIG. 2 includes various embodiments including single and multiple SMP systems. FIG. 2(a) includes an expandable aneurysm implant including multiple linked expandable elements (e.g., SMP foam). Expandable foam elements 201, 202, 203 (shown in expanded form) are spaced along a single carrier element 205 (e.g., a backbone) extending axially through all the expandable foam elements. FIG. 2(b) links SMP elements 210, 211, 212 (shown in expanded form) together via linking elements 215, 216. No single backbone extends through all the elements of FIG. 2(b).

FIG. 2(c)(i) shows how chain-like structure 220 maintains flexibility despite having elements 225, 226, 227 in compressed form. Compressed elements 225, 226, 227 are stiff and may present problems when navigating the twists and turns of patient vasculature (e.g., small cranial vasculature). However, spaces 228, 229 and the like allow system 220 to bend and adapt to the twists and turns of patient vasculature, despite the stiffness of the compressed SMP foam. FIG. 2(c)(ii) shows elements 225, 226, 227 in expanded form with the backbone and the elements in their primary states and deployed in a patient. The backbone may include, for example, a shape memory alloy (e.g., Nitinol) that has primary and secondary states.

Figure 2D:
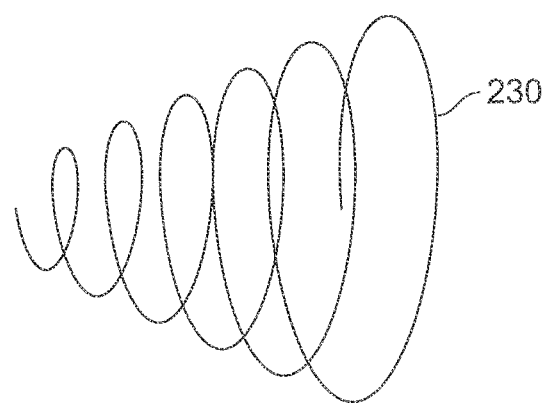
Figure 2E:
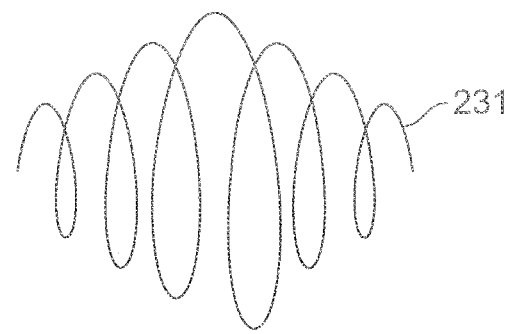
Figure 2F:
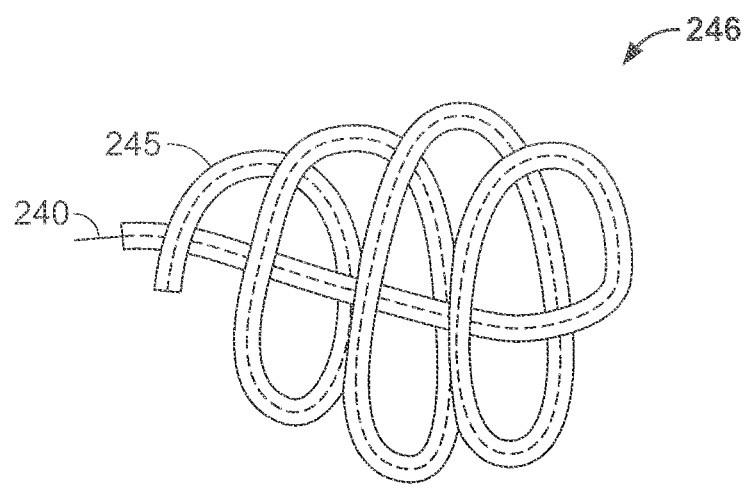
Figure 3A:
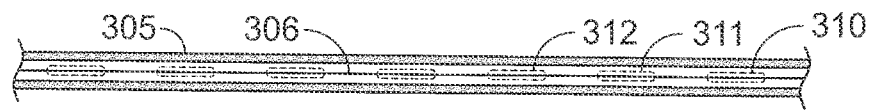
FIGS. 3A-D include embodiments in compressed pre-delivery stage and uncompressed, expanded post-delivery stage.
Figure 3B:
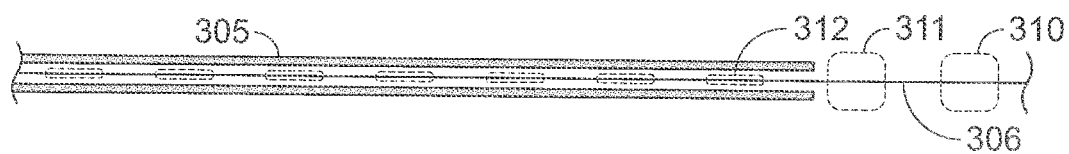
Figure 3C:
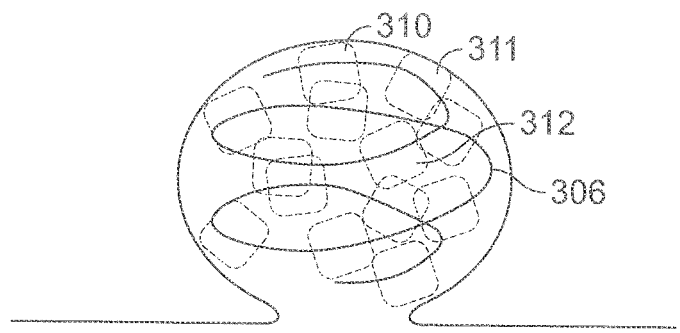
Figure 3D:
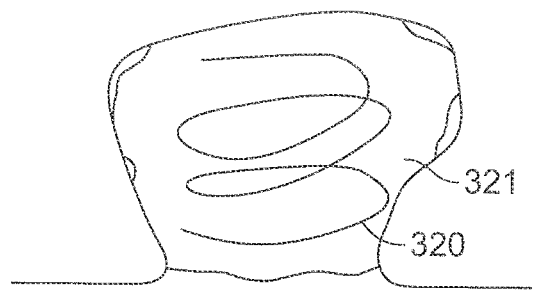

FIGS. 2(d) and 2(e) show backbones 230, 231 that are just two of the many configurations backbones may take in their relaxed primary states. Backbones 230, 231 may couple to numerous shorter elements (e.g., FIG. 2(c)) or one or more longer elements (e.g., FIG. 2(f)). For example, FIG. 2(f) shows backbone 240 coupling to elongated, monolithic element 245 (e.g., greater than 5 cm in length). Depending on stiffness of backbone 240 and element 245, system 246 may still maintain the requisite level of stiffness that facilitates advancing element 245 through a deployment catheter while being flexible enough to navigate the twists and turns of small vasculature.

FIG. 3 includes various embodiments in compressed pre-delivery stage and uncompressed, expanded post-delivery stage. FIG. 3(a) shows expandable foam elements 310, 311, 312 coupled to backbone 306 and compressed radially (i.e., secondary state) for endovascular delivery through microcatheter 305. FIG. 3(b) shows elements 310, 311 deployed from catheter 305 and expanded back to their primary state. FIG. 3(c) shows a series of linked elements expanded within an aneurysm. FIG. 3(d) shows an embodiment where both single monolithic SMP 321 and backbone 320 are both expanded into their respective primary states after being delivered into an aneurysm.

FIG. 4 includes an embodiment with spacers located between expandable elements. In FIG. 4(a) expandable foam elements 401, 402, 403 (shown in expanded form) are coupled to carrier element 410 (e.g., backbone) and separated from one another by wire coil spacers 421, 422. Wire coil spacers 421, 422 may be monolithic with carrier element 410 (e.g., wire coiled spacers 421, 422 and carrier element 410 may be formed of a single wire or rod that is straight at some sections and coiled at others). In other embodiments, wire coil spacers 421, 422 may be loosely and non-fixedly coupled to carrier element 410. In other embodiments, wire coil spacers 421, 422 may be fixedly coupled (e.g., welded) to carrier element 410. FIG. 4(b) shows the system of FIG. 4(a) included within catheter 430 with expandable foam elements 401, 402, 403 shown in compressed secondary form. Spacers 421, 422 are coaxial with carrier element 410. As seen in FIG. 4(b) the outer diameter of spacers 421, 422 is equal to the compressed outer diameter of expandable foam elements 401, 402, 403. Use of such spacers may facilitate pushing the SMP chain through a catheter. In other words, without the spacers there may be bunching between the SMP elements, which could frustrate advancement of the elements through the patient's vasculature.

Figure 5:
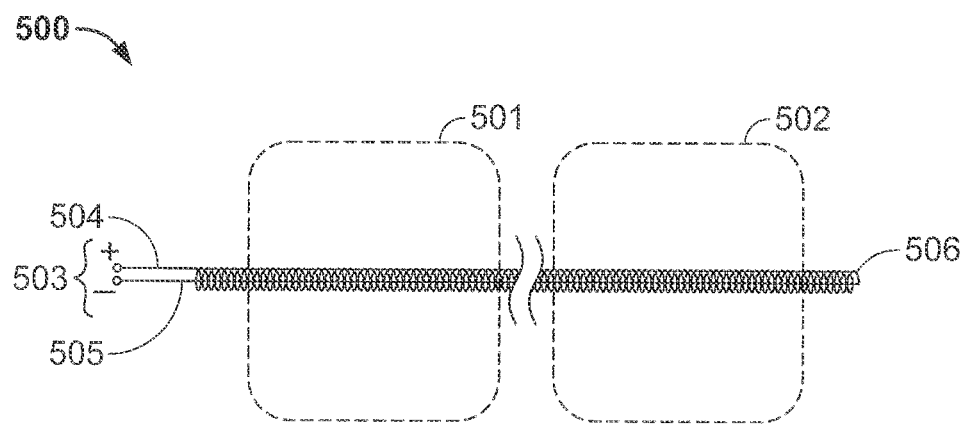
FIG. 5 includes a heated carrier embodiment.

FIG. 5 includes a heated carrier embodiment 500. Resistively heated carrier element 503 includes inner wire 505 and outer wire coil 504 coupled together at distal end 506 to complete an electronic circuit. Expandable foam elements 501, 502 are shown in expanded form. In this embodiment, a pushing element (not shown) containing two conductors couples an external power supply to carrier 503. Current may flow from the power supply to carrier 503 to cause resistive heating of elements 501, 502 to thereby transform elements 501, 502 from their secondary states to their primary states.

Figure 6:
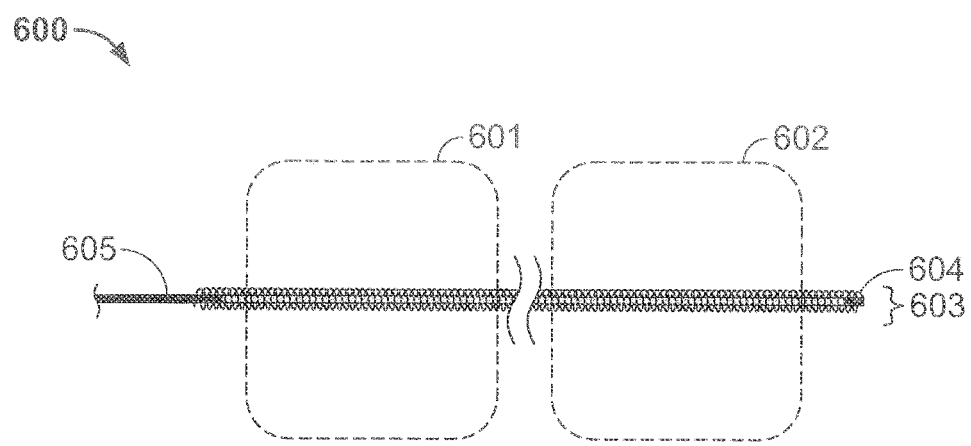
FIG. 6 includes an embodiment with a fiber optic light diffuser delivery mechanism.

FIG. 6 includes an embodiment 600 with a fiber optic light diffuser. Carrier element 603 includes inner flexible fiber optic light diffuser 605 and outer wire coil 604. The fiber optic light diffuser 605 is coupled to an external light source, such as a laser (not shown). Laser energy is absorbed by outer wire coil 604, resulting in the heating of coil 604, causing expandable foam elements 601, 602 to expand to their primary states.

Figure 7:
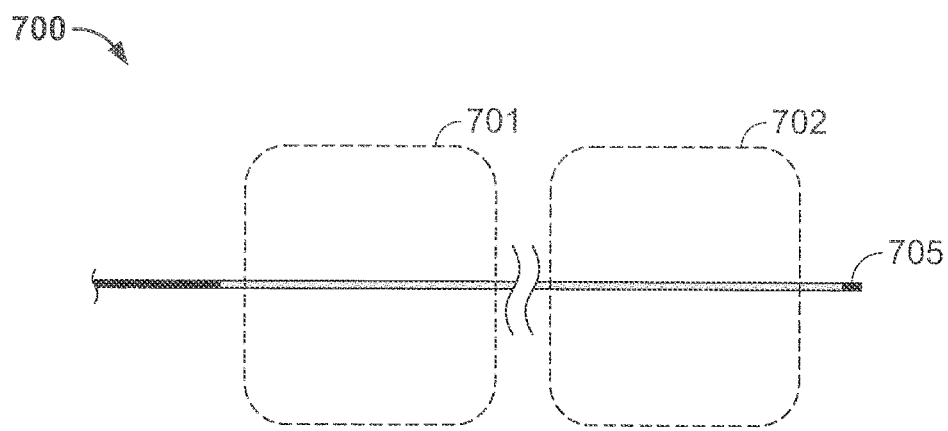
FIG. 7 includes an embodiment with a fiber optic light diffuser delivery mechanism.

FIG. 7 includes an embodiment 700 with a flexible fiber optic light diffuser. The carrier element includes flexible fiber optic light diffuser 705. The fiber optic diffuser 705 is coupled to an external light source, such as a laser (not shown). Laser energy is absorbed by expandable foam elements 701, 702, resulting in heating of the foams causing the expandable foam elements to expand to their primary states.

Figure 8A:
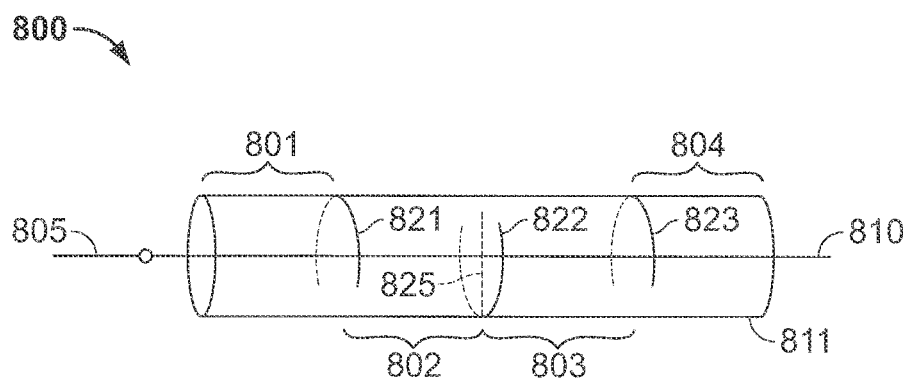
FIGS. 8A-B include a flexible embodiment of a monolithic SMP device.
Figure 8B:
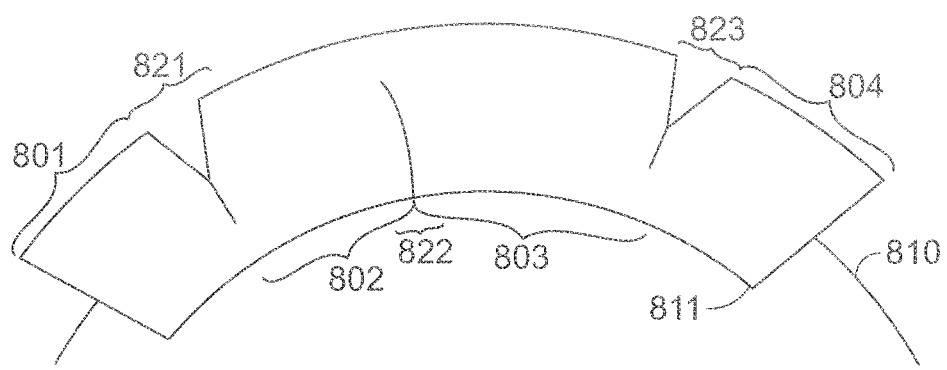

FIG. 8 includes a flexible embodiment for a foam configuration. In FIGS. 8(*a*) and 8(*b*), system 800 includes backbone 810, which is coupled to guide wire (e.g., pusher wire) 805. Backbone 810 includes primary and secondary states. For example, backbone may be formed from nickel titanium (e.g., Nitinol). FIG. 8(*a*) shows backbone 810 in its secondary state and FIG. 8(*b*) shows backbone 810 in its primary state. Monolithic SMP 811 (formed of a single piece of foam) covers a majority (>50%) of backbone 810. SMP 811 includes primary and secondary states, first and second portions 802, 803, and a first joint 822 located between the first and second portions.

In a first configuration as shown in FIG. 8(*a*), backbone 810 is coupled to pusher wire 805. SMP 811 and backbone 810 are both in their respective secondary states. In this configuration, system 800 is configured to be advanced through vasculature. For example, first and second portions 802, 803 are generally collinear with one another as well as with portions 801, 804. Joints 821, 822, 823 are generally closed. However, joints 821, 822, 823 allow for flexibility as system 800 navigates through curves in the vasculature.

In a second configuration as shown in FIG. 8(*b*), backbone 810 is decoupled from the pusher wire (not shown), and monolithic SMP 811 and backbone 810 are both in their respective primary states and configured to both be included in an aneurysm. (Only a portion of the SMP is shown, and a longer version may look more like FIG. 2(*f*).) For example, SMP 811 is expanded to fill, partially or fully, a void such as an aneurysm. Backbone 810 may transform from its secondary state (primarily straight or uncoiled) to its secondary state (coiled into a helix or coil such as shown in FIGS. 2 (*d*), (*e*), and (*f*). As seen in FIG. 8(*b*), first and second portions 802, 803 are non-collinear with one another based on first portion 802 pivoting about first joint 822 relative to second portion 803. Also, portion 804 is pivoted about joint 823 and portion 801 is pivoted about joint 821.

Joints 821, 822, 823 may include slits, which is broadly used herein to include, for example, an aperture, cut, slice, compression, notch, cleft, breach, cleavage, fissure, and/or split. As seen in FIG. 8(*a*), slit 822 includes a long axis 825 that is generally perpendicular to a long axis of backbone 810 (which runs the length of backbone 810). Also, slit 822 extends less than 360 degrees about backbone 810. In FIG. 8(*a*) slit 822 extends approximately 320 degrees about the backbone but other embodiments may extend, for example, 50, 100, 150, 200, 250, 300 degrees and the like. In an embodiment, slits may extend a full 360 degrees about backbone 810 but not extend from the exterior surface of SMP 811 all the way to backbone 810, thereby keeping 811 monolithic with portions 801, 802, 803, 804 not completely severed from one another.

As shown in FIG. 8(*a*), slit 821 is included in a superior exterior surface of SMP 811 and slit 822 is distal to slit 821 and included in an inferior exterior surface of SMP 811 but not the superior exterior surface of the monolithic SMP. Thus, the slits are staggered to allow for flexibility while maintaining SMP 811 as monolithic (considering slits 821, 822, 823 do not completely sever portions 801, 802, 803, 804 from one another).

In an embodiment, SMP 811 is greater than 5 cm in length and is the only SMP coupled to backbone 810. In other embodiments the only SMP coupled to the backbone may be longer or shorter and include lengths of, for example, 3, 4, 6, 7, 8, 9 cm and the like.

Further, in an embodiment the SMP in the secondary state has a modulus that is greater than the SMP's modulus in the primary state. For example, the SMP is stiffer when being pushed through a catheter and into the body, but softer and more compliant when deployed in an aneurysm and pushed up against delicate aneurysm walls.

In FIG. 8(*a*) in their secondary states all of portions 801, 802, 803, and 804 are flush against one another. This may facilitate smoothly advancing SMP 811 within a catheter as there are no edges exposed to catch on various obstacles that may be encountered during deployment. As shown in FIG. 8(*a*) portion 801 includes a distal face (i.e., distal face formed by slit 821) that is complimentary to and flush against the proximal face of portion 802 (i.e., proximal face formed by slit 821).

However, in FIG. 8(*b*) the portions are not all completely flush against one another due to pivoting (e.g., slit 821 is opened partially). This may expose extra surface area (e.g., inside surfaces of slit 821) to blood flow to facilitate clotting and aneurysm healing.

In one embodiment, SMP 811 fixedly adheres to backbone 810 when both are in their primary states and implanted in a patient. For example, an adhesive may couple SMP 811 to backbone 810 (possibly applied in a thin layer over backbone 810). Such adhesives include, for example, epoxy, urethane, acrylate, methacrylate, urethane acrylate, and the like. Options include adhesives that function either through mechanical adhesion and/or chemical adhesion (e.g., covalent, ionic, polar, or Vander Waals coupling forces). For example, a urethane adhesive may be useful due to its ability to chemically bond to both SMP 811 and backbone 810 (which includes a metal surface in some embodiments). In another embodiment, the adhesive could be SMP 811 itself so SMP fixedly adheres directly to backbone 810. For example, a urethane SMP may adhere directly to backbone 810 without need for an adhesive layer coupling SMP 811 to backbone 810. In other words the urethane of a urethane SMP may provide for coupling to the backbone without an additional adhesive layer because the "wet" urethane functions as an adhesive. In another embodiment, SMP 811 includes a thermoplastic SMP adhesive obtained by heating backbone 811 to the melting point of SMP 811 such that SMP 811 wets backbone 810 and develops a direct bond between SMP 811 and backbone 810. In an embodiment, adhering a cured polymer foam (e.g., the SMP to be used to embolize the aneurysm) to a backbone may be done with a liquid thermoset SMP. The thermoset may be of the same type of foam as the embolizing foam. Thus, a first layer of SMP adheres to the backbone and then another layer of SMP adheres to the first SMP. The first layer (the thermoset) could be slightly different (e.g., a different Tg) from the second layer SMP and could have additives that benefit the application (e.g., radio opaque particles like tungsten).

In another embodiment, backbone 810 may be sufficiently bonded or fixed to SMP 811 through mechanical friction. The basis for the friction force is the friction between SMP 811 and backbone material 810 and the normal stress applied by previously stretched material (such as a axially stretched SMP in its secondary state). Above SMP embodiments that fixedly adhere directly to backbone 810 (when both are in their primary states when implanted in a patient) contrast with, for example, hydrogels that are not adhesive (especially not when "wet" as is the case when implanted in a patient).

Figure 10A:
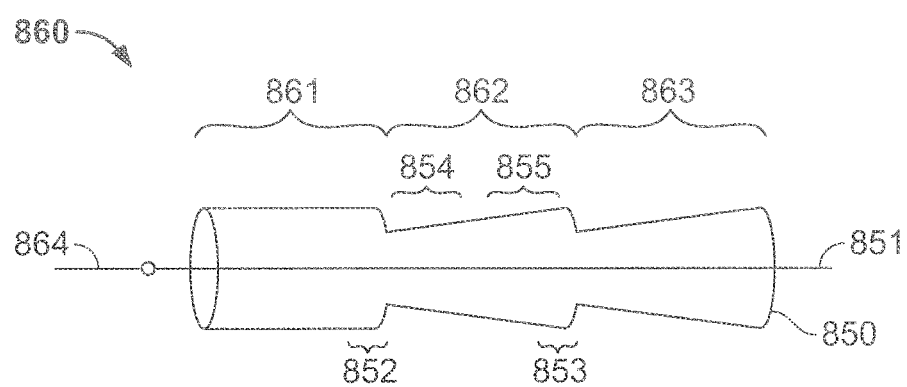
FIGS. 10A-B include a flexible embodiment of a tapered monolithic SMP device.
Figure 10B:
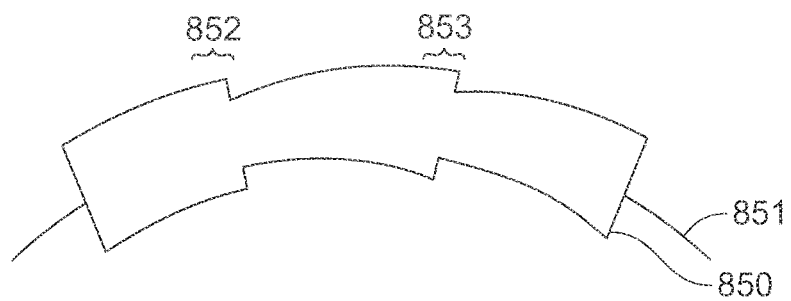

FIGS. 10 (*a*) and (*b*) include embodiments similar to FIG. 8 in that SMP 850, located on backbone 851 which is coupled to pusher elements 864, is monolithic and comprised of portions 861, 862, 863; none of which are completely severed from one another. Joints 852, 853 allow portions 861, 862, 863 to pivot with regard to one another. Pivoting may be facilitated considering portion 862 includes a face that tapers from a relatively thinner proximal portion 854 to a relatively thicker distal portion 855. The tapering may facilitate the ability to retract foam 850 back into a catheter if, for example, SMP 850 is properly placed in an aneurysm but then becomes improperly placed outside the aneurysm. If SMP 850 has already begun to expand the tapered portions facilitate retracting the SMP back into the catheter.

Figure 11:
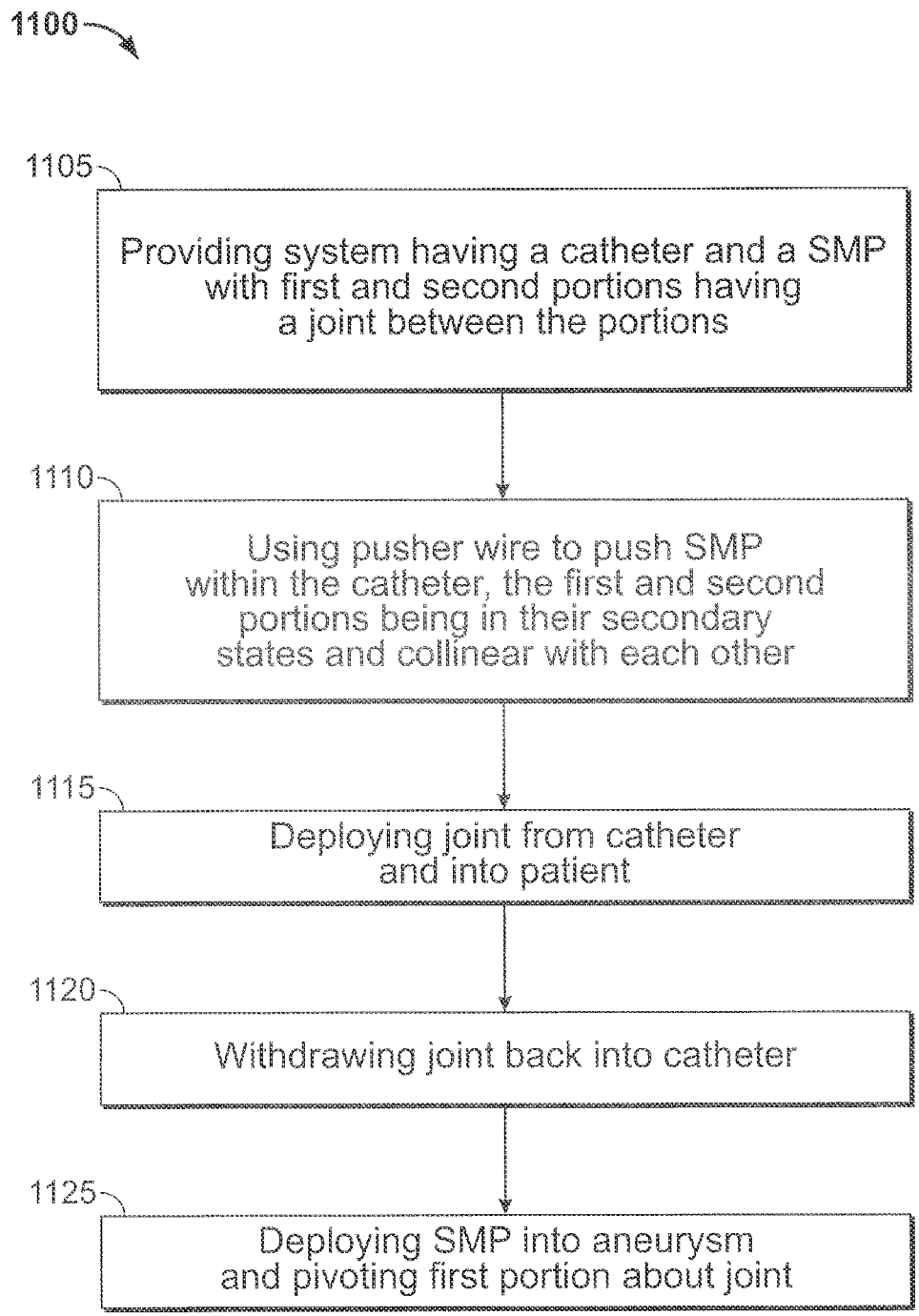
FIG. 11 includes a process for embolization of an aneurysm in an embodiment.

FIG. 11 includes process 1100 in an embodiment of the invention. Block 1105 provides a system comprising a backbone (the backbone being coupled to a pusher wire and including primary and secondary states) and a catheter. A SMP, which covers a majority of the backbone, may be deployed within the catheter. The SMP may be a monolithic SMP including: (a) primary and secondary states, (b) first and second portions, and (c) a first joint located between the first and second portions.

Block 1110 includes advancing the system through a patient's vasculature, using a pusher wire that is coupled to the backbone. For example, the catheter may be placed in the aneurysm and then the backbone/SMP are advanced through the catheter. While doing so, the monolithic SMP and the backbone are both in their respective secondary states, and the first and second portions are generally collinear with one another.

Block 1115 includes deploying the first joint from the catheter and into the patient. Block 1120 includes withdrawing the deployed first joint from the patient and back into the catheter. Block 1120 may be necessary if the SMP becomes misplaced. Various configurations, such as the configuration of FIGS. 8, 9, 10, may facilitate the ability to withdraw the jointed sections back into the catheter.

Block 1125 includes locating the monolithic SMP and the backbone, both in their respective primary states, in an aneurysm, the first and second portions being non-collinear with one another based on the first portion pivoting about the joint relative to the second portion.

Figure 9A:
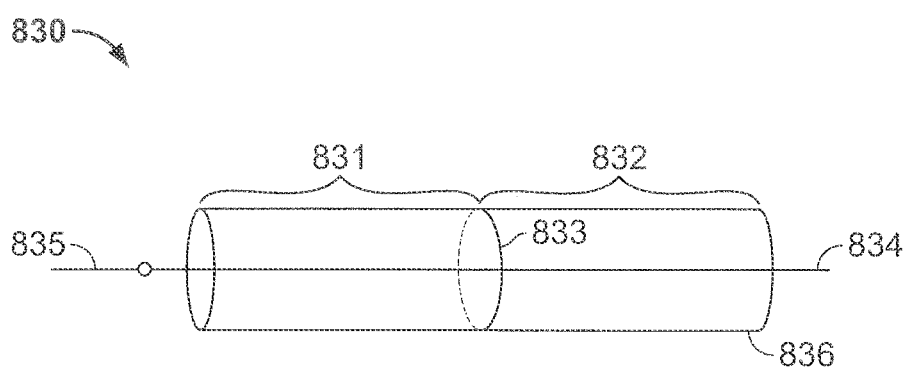
FIGS. 9A-B include a flexible embodiment of a SMP device.
Figure 9B:
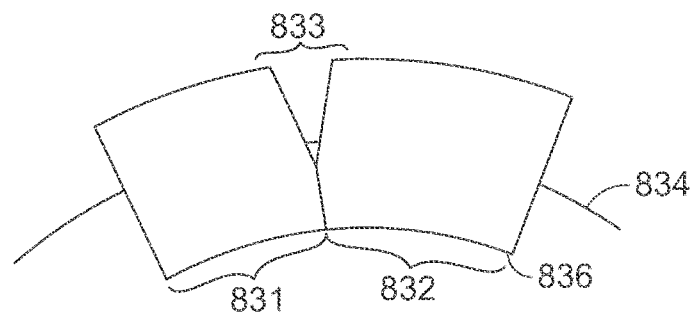

FIGS. 9A-B include an embodiment having a flexible SMP 836. Specifically, backbone 834 includes primary and secondary states. SMP portions 831, 832 collectively cover a majority of the backbone that couples to pusher element 835. Portions 831, 832 each include primary and secondary states. Joint 833 is located between portions 831, 832. In a first configuration (FIG. 9(*a*)) portions 831, 832 and backbone 834 are all in their respective secondary states and configured to be advanced through vasculature. In a second configuration (FIG. 9(*b*)) portions 831, 832 and backbone 834 are all in their respective primary states and configured to all be included in an aneurysm. In the second configuration portion 831 pivots about joint 833, with respect to portion 832, when portions 831, 832 and backbone 834 are all in their respective primary states. At least part of portion 831 is flush against at least part of portion 832 when in the first configuration. In FIG. 9(*a*) portions 831, 832 are completely flush against each other. This portion 831 face being flush to a portion 832 face may facilitate deployment of the SMP portions through a catheter or sheath. This may also facilitate withdrawal of the SMP portion 831, 832 back into the catheter or sheath if the portions are misplaced (e.g., in a parent artery).

FIG. 9(*a*) only shows two portions but certainly more portions and more joints may be included. In an embodiment, portions 831 and 832 are completely severed from one another. However, in another embodiment portions 831, 832 are not completely severed from one another and instead are part of a single monolithic SMP. Such an embodiment may include a deep cut to form joint 833. The cut may be deep but not surround backbone 834 by 360 degrees and/or may not extend all the way to backbone 834. Either or both of portions 831, 832 may be fixedly coupled to backbone 834. However, one or both of portions 831, 832 may be non-fixedly coupled (e.g., slidably coupled) to backbone 834.

An embodiment includes a system comprising a backbone including primary and secondary states; and a monolithic SMP covering a majority of the backbone. The SMP includes first and second portions. The SMP pivots the first portion about the second portion when the monolithic SMP and the backbone are both in their respective primary states and also when the monolithic SMP and the backbone are both in their respective secondary states. Thus, in one embodiment the backbone and SMP may include a stiffness configured to allow flexibility and pivoting when traversing the patient's vasculature. However, the stiffness may still be such that when the backbone and SMP are in their primary states (e.g., when deployed into an aneurysm and expanded) the portions of the SMP may pivot about one another as the backbone takes its shape (e.g., helical shape) and/or the elements expand. In such a situation the SMP may not necessarily include joints such as those found in FIGS. 8, 9, and 10. Instead, the SMP may, for example, be in the shape of a simple solid cylinder that runs along a majority of the backbone. The backbone may be centered within the cylinder. FIG. 2(*f*) includes an example of a jointless SMP that covers a majority (>50%) of a backbone.

The SMP foam elements described herein may be cylindrical, ellipsoidal, spherical, diamond or other shape in their expanded form. The expandable foam elements may be identical or may have different shapes, sizes, and/or spacing within a single device. For example, different portions of a single SMP may have different shapes (such as portions 861 and 862 of FIG. 10(*a*)). This also applies to devices with several different foams in a single device (e.g., FIG. 2(*a*)).

As shown above, a device may contain any number of foam elements (FIG. 2 (*c*)), including a single foam element along the entire length (or a majority of the length) of the carrier element (FIG. 2(*f*)). The shape of the single foam element may be patterned to retain flexibility in the compressed state while permitting retraction back into the microcatheter after expansion. This patterning may include the use of joints as described in regards to FIGS. 8-10. Another example of patterning is to include alternating diamonds of foam. In a given length of the SMP there may be two diamonds on opposite sides. The adjoining sections, both proximal and distal (to non-terminal segments) have two diamonds rotated by 90 degrees with the axial points of the diamonds overlapping. A similar pattern may be applied in the case of multiple foam elements.

Some embodiments may avoid or limit axially abrupt changes in diameter/materials along the length of the device that could catch on the edge of the microcatheter during retraction (e.g., FIG. 10).

In one embodiment, the expandable foam elements are spaced along a single carrier element extending axially through all the expandable foam elements. The carrier element may be comprised of a wire filament (e.g. Nitinol), a GDC-like wound wire coil, or a combination of both. Alternatively, the carrier element may be a polymer strand, and specifically may be a SMP. The carrier element may assume a straightened form during endovascular delivery through a microcatheter. The carrier element may assume a helical or other complex 3D shape when delivered out of the microcatheter and into the aneurysm. The expandable foam elements may be bonded to the carrier element to maintain their spacing. The spaces between expandable foam elements may be occupied by cylindrical flexible spacer elements having the same outer diameter as the foam elements in their compressed form. The flexible spacer elements may be wire coils (see above), SMP foam, or other flexible material. In another embodiment, the carrier element may consist of alternating straight and coiled sections with the expandable foam elements placed over the straight sections and the coiled sections serving as spacers (See FIG. 4).

The expanded foam in various embodiments acts a scaffold for clot formation within the open celled SMP structure. The scaffold nature of the foam may work with the body's healing response to initially clot, endothelialize the neck of the aneurysm, and, finally, remodel the clot with extra cellular matrix (including collagen). Throughout this healing process, the SMP scaffold stabilizes the treated aneurysm and permits the natural healing process to occur. In contrast, metallic coils provide minimal support to the large volume of clot that surrounds them (clots typically make up 60-90% of the total aneurysm volume), and hydrogels block out clotting and normal healing with their small pore structure. The scaffold nature of the foams is beneficial in healing of aneurysms.

The SMP foam may expand spontaneously upon delivery into the aneurysm (e.g. Tg≤body temperature) or may require an external energy source to achieve expansion (e.g., laser heating, resistive heating, heated fluid flush, inductive heating, and the like). If an external energy source is used, the device may be retracted back into the microcatheter if necessary prior to expansion. In one embodiment, the carrier element serves as a resistive heater by passing a current through the carrier element (See FIG. 5).

In an embodiment, all or part of the carrier element is comprised of magnetic material and is heated inductively by an external magnetic field. In an embodiment, the expandable foam elements are doped with magnetic particles and heated inductively by an external magnetic field. In an embodiment, a flexible fiber optic light diffuser is positioned inside the carrier element (e.g., FIGS. 6, 7); the carrier element absorbs the laser light and is heated, which in turn heats the expandable foam elements. In an embodiment, the expandable foam elements are doped with laser absorbing dye or particles and a flexible fiber optic light diffuser serves as the carrier element (FIGS. 6, 7); the doped expandable foam elements absorb laser light and are heated.

In the case of a heated carrier element comprised of a polymer strand, the polymer strand may be doped with conductive particles (e.g. carbon, metallic, etc.) distributed to form a current path for resistive heating of the polymer strand. Alternatively, the polymer strand may be doped with magnetic particles for inductive heating or laser absorbing dye/particles for laser heating.

A degradable membrane may be used to encapsulate/restrain the compressed foam elements during endovascular delivery, facilitating transport through the microcatheter and retraction back into the microcatheter if placement in the aneurysm is not satisfactory. The membrane may be comprised of a water or blood soluble/degradable polymer, thermally degradable polymer, or otherwise degradable material. Thermal degradation may be accomplished spontaneously at body temperature or at higher temperature by a heated fluid flush or other heating mechanism (e.g., laser heating, resistive heating, electromagnetic heating, or inductive heating). The membrane may be applied over the compressed expandable foam elements by dip-coating or other suitable means, or the membrane may be a tubular form in which the compressed device can be inserted. Bioactive (e.g. clotting) agents may be incorporated into any part of a device, including the expandable foam elements, the carrier element or linking elements, or the degradable restraining membrane, to enhance the healing response.

Above much discussion has been made regarding various malformation filling devices (e.g., SMP foam) that are implanted in a patient. Discussion now turns towards devices and systems for implanting malformation filling devices (e.g., SMP devices).

Figure 12A:
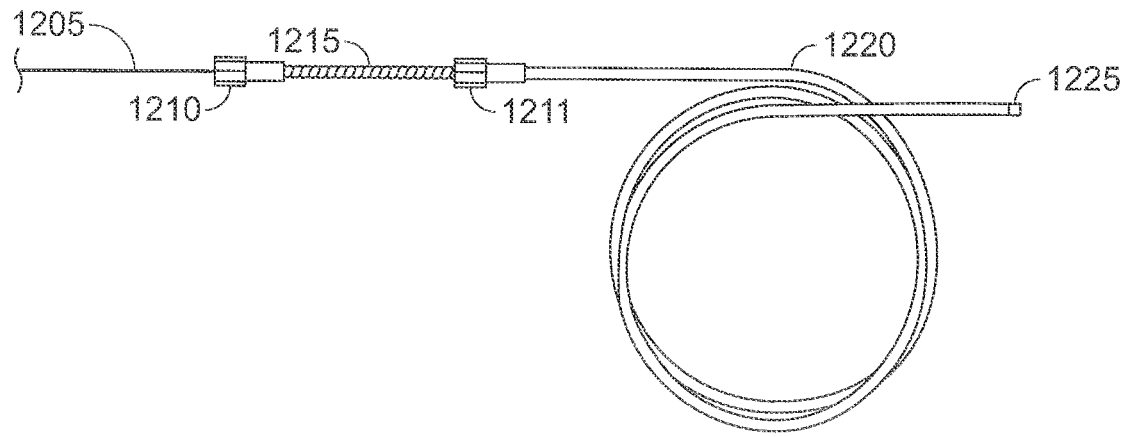
FIGS. 12A-B include an embodiment comprising a microcatheter, collar, and sheath.
Figure 12B:
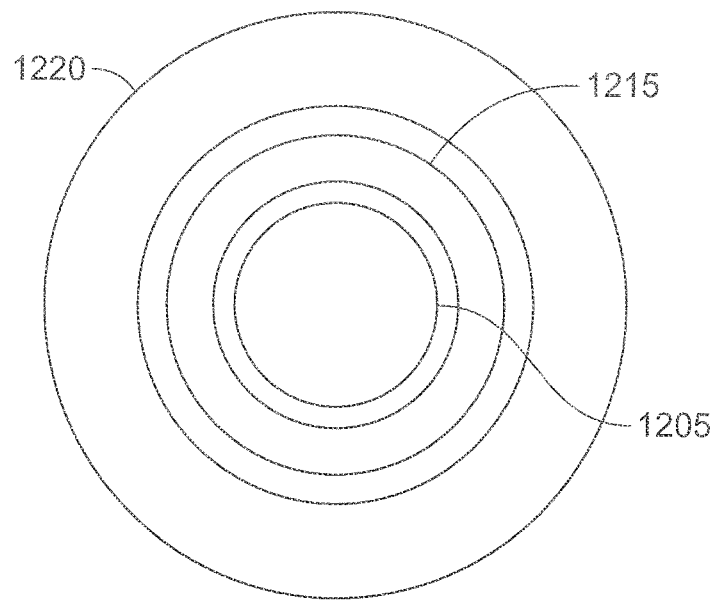

An embodiment provides a system for endovascular delivery of an expandable implant to embolize an aneurysm. FIG. 12 includes an embodiment comprising microcatheter 1220, lumen-reducing collar 1225 coupled to the distal tip of microcatheter 1220, flexible pushing element 1205 detachably coupled to an expandable implant (e.g., SMP foam), and flexible tubular sheath 1215 inside of which the compressed implant and pushing element are pre-loaded.

By preloading the SMP implant within the sheath, the sheath can more easily slide within the microcatheter (along with the SMP inside the sheath) than would be the case if the SMP foam were to be forced to slide along the inside of the microcatheter (i.e., with no sheath buffer between the foam and the stationary microcatheter that has already been located in the aneurysm before the implant is introduced into the patient). Sliding the SMP foam along the inside of the catheter may be difficult considering the friction between the microcatheter and the SMP foam. Thus, the flexible tubular sheath facilitates transport of the compressed expandable implant through the microcatheter. In one embodiment, by advancing the flexible tubular sheath out of the microcatheter with the expandable implant still inside the sheath, the flexible tubular sheath provides the ability to assess the stability of the microcatheter position prior to deployment of the expandable implant, which potentially may not be retracted once deployed. If the microcatheter moves out of proper position while the flexible tubular sheath (with the compressed expandable implant still inside) is advanced beyond the distal tip of the microcatheter, the sheath can be retracted to allow re-positioning of the microcatheter. Also, the flexible tubular sheath may be used to restrain the compressed expandable implant. In conventional systems the compressed implant is restrained solely by the microcatheter itself.

Using standard fluoroscopic interventional techniques, the distal tip of the microcatheter is positioned in the neck of the aneurysm. The flexible tubular sheath 1215 (containing the flexible pushing element 1205 and an expandable implant) is passed through the microcatheter until it is stopped by lumen-reducing collar 1225. Flexible pushing element 1205 is then advanced distally until the expandable implant emerges from flexible tubular sheath 1215 and is delivered into the aneurysm. Finally, the expandable implant is detached from flexible pushing element 1205 using suitable means (electrical, mechanical, optical, and the like) coupled to the system.

Figure 13A:
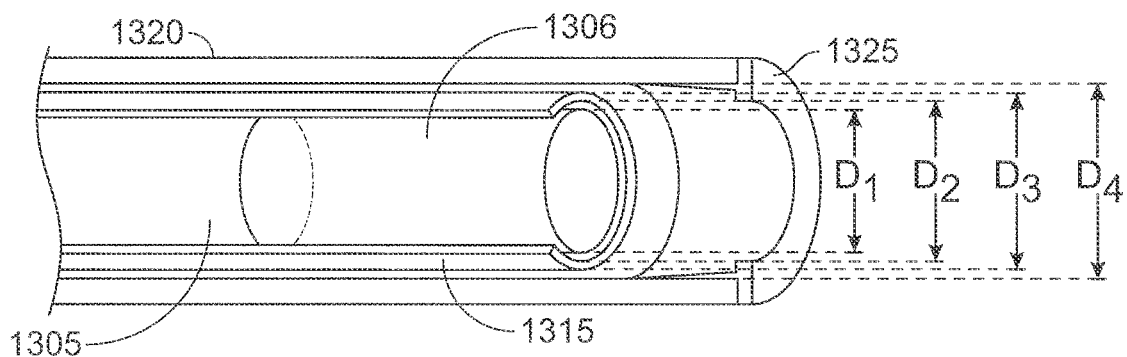
FIGS. 13A-C include stages of delivery for embolization of an aneurysm in an embodiment.
Figure 13B:
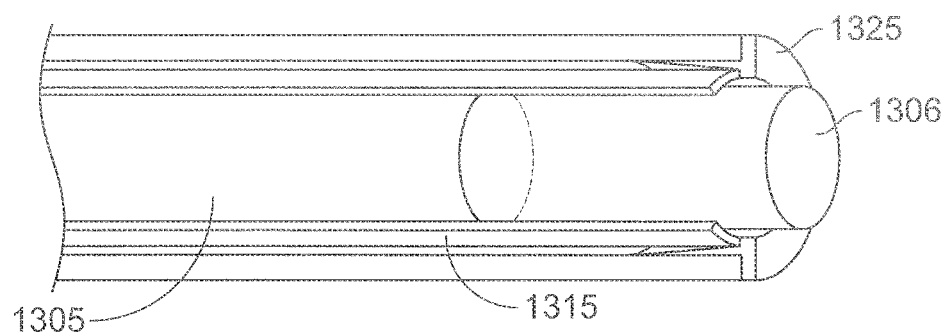
Figure 13C:
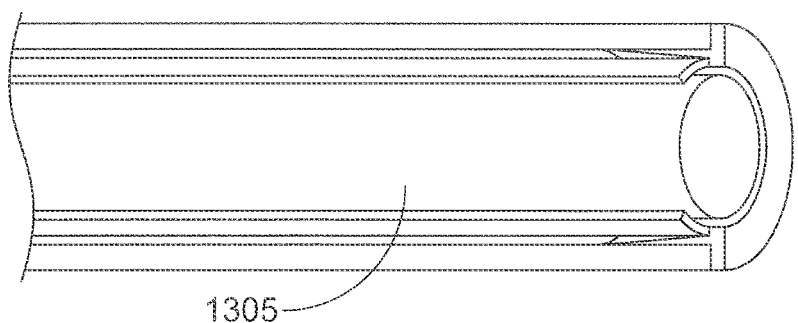
Figure 14A:
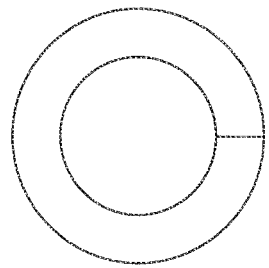
FIGS. 14A-B include various embodiments for a sheath.
Figure 14A:
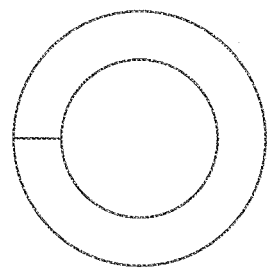
Figure 14A:
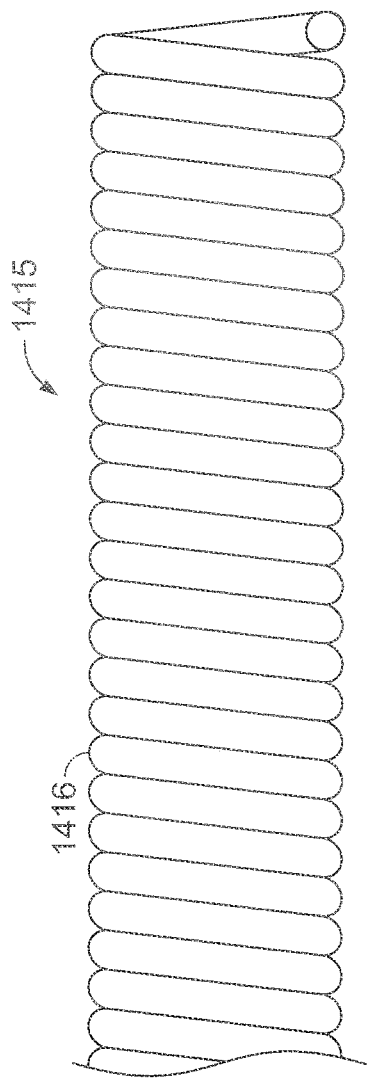
Figure 14B:
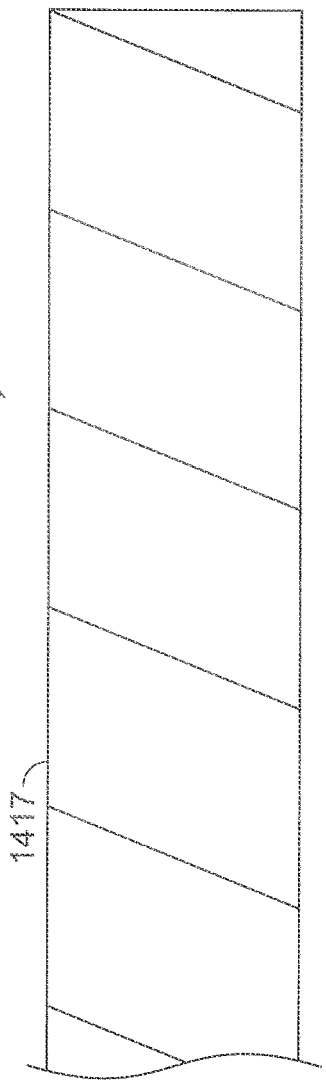

FIG. 13 includes stages of delivery for one embodiment of the invention. FIG. 13(*a*) includes pushing element 1305 pushing implant 1306 along with (i.e., simultaneously) sheath 1315, all within microcatheter 1320. Expandable implant 1306 is contained inside flexible tubular sheath 1315. FIG. 13(*b*) shows collar 1325 blocking sheath 1315 while implant 1306 continues to be pushed by pushing element 1305. Implant 1306 is pictured moving while sheath 1315 is stationary. In other words, pushing element 1305 and flexible tubular sheath 1315 are advanced through microcatheter 1320 until the sheath is stopped by lumen-reducing collar 1325. The pushing element continues to advance causing the expandable implant to emerge from the sheath and the microcatheter. FIG. 13(*c*) shows pushing element 1305 near the distal end of catheter 1320, with implant 1306 deployed from catheter 1320 and decoupled from pusher element 1305.

Returning to FIG. 12, manual clamping fixture 1211 (e.g., O-ring compression fitting) is included on the proximal end of microcatheter 1220 to fix the position of inner flexible tubular sheath 1215. Second manual clamping fixture 1210 is incorporated on the proximal end of flexible tubular sheath 1215 to fix the position of inner pushing element 1205. The clamping fixtures can be opened to allow movement of the inner components as necessary.

Thus, FIG. 12 provides an apparatus for endovascular delivery of an expandable implant into an aneurysm. The lumen-reducing collar at the distal tip of the microcatheter stops the flexible tubular sheath, in which the pushing element and expandable implant are pre-loaded, while allowing the expandable implant to exit the microcatheter. The clamping fixture at the proximal end of the microcatheter may be used to fix the position of the flexible tubular sheath. The clamping fixture at the proximal end of the flexible tubular sheath may be used to fix the position of the pushing element.

In one embodiment one or more radiopaque markers (e.g., platinum bands) are incorporated into the distal portion of microcatheter 1220 to facilitate navigation under fluoroscopy. Lumen-reducing collar 1225 may serve as one of the markers. Pushing element 1205 may be entirely radio-opaque to enable fluoroscopic visualization of its position. Flexible tubular sheath 1215 may not be 100% radio-opaque so it does not obscure the pushing element. The expandable foam element(s) themselves may be radio-opaque by incorporating radio-opaque elements (atomically or as particles) into a polymer used for the foam during the foam formulation process. The backbone and/or linking elements (see FIG. 2(*b*)) may also be radio-opaque.

As indicated above and as indicated in FIG. 13, a purpose of flexible tubular sheath 1315 is to allow pre-loading of compressed expandable implant 1306 within sheath 1315. This removes the need to pass compressed expandable implant 1306 through the entire length of microcatheter 1320 with no buffer between foam 1306 and catheter 1320. Because in one embodiment the compressed expandable implant 1306 is pre-loaded at the distal end of flexible tubular sheath 1315, its deployment into the aneurysm only requires pushing it (in relation to sheath 1315) a relatively short distance (e.g., length of the compressed expandable implant).

Further regarding FIG. 13, lumen-reducing collar 1325 may serve to prevent (1) flexible tubular sheath 1315 from exiting microcatheter 1320, and (2) axial stretching of flexible tubular sheath 1315 as pushing element 1305 is advanced to deliver expandable implant 1306.

FIG. 14 includes various embodiments for a sheath in an embodiment of the invention. Flexible tubular sheath 1415 may include metal round wire coil 1416, metal ribbon (flat) wire coil 1417, and the like.

In an embodiment, a flexible tubular sheath may be comprised of multiple sections, each section decreasing in stiffness from proximal to distal. For example, a two-section sheath may be comprised of a proximal solid metal tube and a distal metal ribbon wire coil. A thin polymer coating may be applied over the metal to inhibit axial (i.e., lengthwise) stretching of the coil. As another example, the sheath may include an intermediate portion centrally located between a proximal end portion of the sheath and the distal end portion of the sheath, and the distal end portion of the sheath may be more flexible than the intermediate portion of the sheath.

FIG. 15 includes an embodiment having a stop collar. In FIG. 15 (*a*) the flexible tubular sheath has been partially advanced. In FIG. 15 (*b*) the flexible tubular sheath has reached maximum advancement. The stop-collar may mitigate the potential inability to recapture the expandable implant after it has emerged from the flexible tubular sheath. A stop-collar is positioned on the flexible tubular sheath such that the sheath may advance a fixed distance before or beyond the distal tip of the microcatheter. For example, stop-collar 1525 is located on the outside of the proximal end of flexible tubular sheath 1515 such that sheath 1515 cannot advance beyond the distal tip of the microcatheter 1520 (see FIG. 15(*b*)) due to cinching element 1511. If flexible tubular sheath 1515 is constructed such that it is not susceptible/not highly susceptible to axial stretching (e.g., polymer-coated metal wire coil), the need for lumen-reducing collar 1325 (as shown in FIG. 13) may be diminished. Similarly, a stop-collar may be located on pushing element 1505 (to interface cinching element 1510) such that the detachment point between pushing element 1505 and an expandable implant is near the distal end of flexible tubular sheath 1515 after the expandable implant is delivered into the aneurysm lumen.

Thus, in one embodiment a stop-collar on a flexible tubular sheath may be used instead of a lumen-reducing collar at the distal tip of the microcatheter. The lumen-reducing collar, stop collar, or combinations thereof may all prevent advancing the sheath from extending beyond (fully or partially) the distal tip of the microcatheter.

Figure 16I:
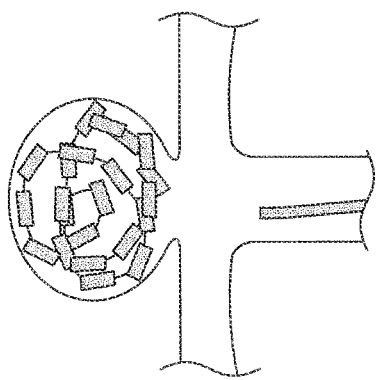
Figure 16H:
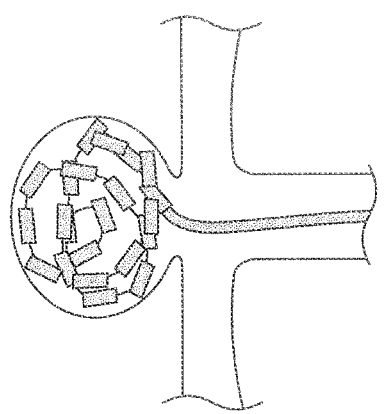
Figure 16G:
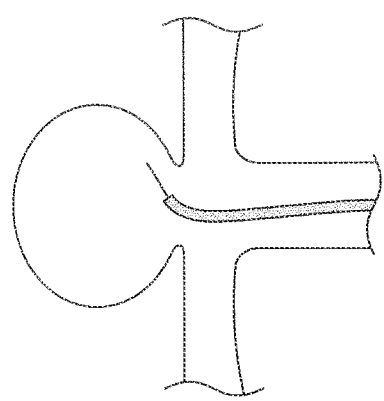

FIG. 16 includes an embodiment for repositioning a misplaced system. As addressed above in regards to FIG. 12, the sheath allows for repositioning a misplaced system. Along these lines, FIGS. 16(*a*)-(*c*) depict locating guide wire 1601 and then microcatheter 1620 within an aneurysm. Flexible tubular sheath 1615 and its contents (e.g., expandable implant and detachably coupled flexible pushing element) are advanced through microcatheter 1620. More specifically, in FIG. 16 (*a*) the guide wire is advanced into the aneurysm; in FIG. 16 (*b*) the microcatheter is advanced along the guide wire into the aneurysm; and in FIG. 16 (*c*) the guide wire is withdrawn. In FIG. 16(*d*) microcatheter 1620 moves out of the aneurysm neck during advancement of flexible tubular sheath 1615, and sheath 1615 is mistakenly advanced into the parent artery instead of the aneurysm lumen. For example, the flexible tubular sheath (containing the expandable implant) is passed through the microcatheter and improperly advanced into the parent vessel instead of the aneurysm due to instability of the microcatheter.

To remedy the situation sheath 1615 and its contents are retracted back into microcatheter 1620 and fully withdrawn from catheter 1620. Then guide wire 1601 is re-inserted and repositioned in the aneurysm, followed by repositioning catheter 1620 along the guide wire in the aneurysm (FIGS. 16(*e*) and (*f*)). The guide wire is withdrawn and the flexible tubular sheath 1615 (containing the expandable implant) is passed through the microcatheter and properly advanced into the aneurysm (FIG. 16(*g*)). In FIG. 16(*h*) one or more embolizing elements (e.g., SMPs) are deployed and the backbone/pusher rod coupling is severed in FIG. 16 (*i*) (i.e., the expandable implant (e.g., backbone) is detached from the pushing element (e.g., pusher rod) and the remainder of the apparatus is withdrawn).

Thus, if the microcatheter moves out of the aneurysm neck after the flexible tubular sheath has been advanced slightly into the aneurysm lumen, and the sheath is still inside the aneurysm lumen, the microcatheter may be re-positioned in the aneurysm neck if necessary, using the protruding sheath as a guide wire. If the microcatheter position is stable following slight advancement of the flexible tubular sheath into the aneurysm lumen, the flexible pushing element may then be advanced distally until the expandable implant emerges from the flexible tubular sheath and is delivered into the aneurysm. The expandable implant is then detached from the flexible pushing element. In the embodiment of FIG. 16, the flexible tubular sheath is constructed such that it is not susceptible to axial stretching (e.g., polymer-coated metal wire coil).

Figure 17:
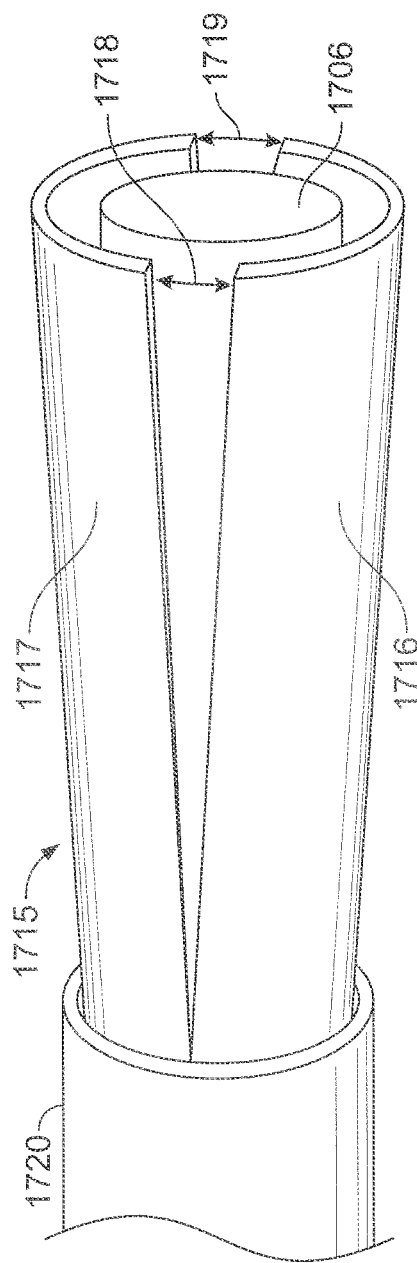
FIG. 17 includes an embodiment with a sheath including apertures.

FIG. 17 includes an embodiment with a sheath including apertures. Flexible tubular sheath 1715 may contain two or more axial slits (e.g., 1718, 1719) extending from the distal tip of the sheath to some point more proximal on the sheath. Slits 1718, 1719 allow sheath 1715 to have members 1716, 1717 that expand when advanced beyond the distal end of the microcatheter 1720. This expansion reduces the friction between expandable implant 1706 and sheath 1715 as the implant is pushed out of the sheath. As another example, the sheath may include an opening, at the distal tip of the sheath, through which the unexpanded implant deploys. The sheath may also include one or more sidewall openings, coterminous with the opening at the distal tip of the sheath, forming one or more branches that expand after deployment from the microcatheter. Including only a single sidewall opening may still allow sufficient expansion to accommodate retrieving the foam (expanded or unexpanded) back into the sheath. In an embodiment, the foam may then be withdrawn back into the catheter.

In an embodiment the flexible tubular sheath may be comprised of a degradable material that is water and/or blood soluble, pH sensitive, and the like. The pushing element may comprise a detachment mechanism to sever or cut the sheath after it is pushed into the aneurysm. The sheath may then degrade within minutes allowing the expandable implant to fully deploy.

In one embodiment, an attachment element exists between the pushing element and expandable implant. The attachment element can be used to pull back, or retrieve, a partially delivered expandable implant. The attachment element can be heated via applied energy (e.g., optical or electric energy) to induce detachment of the expandable implant. The applied energy can also be used to expand the expandable implant prior to detachment at the discretion of the operator (e.g., in the case where the expandable implant requires external energy to induce expansion).

An embodiment of the attachment element includes a polymer section doped with conductive particles. The conductive particles can be selectively heated to heat the attachment element using, for example, electrical current delivered via wires inside the pushing element. If only detachment of the expandable implant is desired, the doping particles (e.g., carbon and/or metallic particles) are distributed throughout the attachment element. If combined expansion and detachment of the expandable implant is desired, the doping particles may be localized so as to make conductive paths between the wires in the pushing element and wires (and/or conductively doped polymer) in the expandable implant.

Again regarding FIG. 13, one embodiment includes a system comprising an unexpanded implant having a maximum outer diameter (D1); a flexible hollow sheath, including a maximum outer diameter (D3), with the unexpanded implant pre-loaded in a distal end portion of the sheath; a flexible hollow microcatheter including a body having a maximum inner diameter (D4); and a collar, coupled to the microcatheter, having a maximum inner diameter (D2). The maximum inner diameter of the microcatheter body (D4) is greater than the maximum outer diameter of the sheath (D3). The maximum outer diameter of the sheath (D3) is greater than the maximum inner diameter of the collar (D2). The maximum inner diameter of the collar (D2) is greater than the maximum outer diameter of the unexpanded implant (D1). Based at least in part on D1, D2, D3, D4, the sheath and pre-loaded unexpanded implant may simultaneously advance within the microcatheter. Advancement of the sheath is eventually halted by the collar. Also, the unexpanded implant may advance past the collar and the halted sheath and into a patient.

In an embodiment, the sheath may be stretchable along its long axis. However, the collar may block advancement of the sheath and lessen axial stretching of the sheath when deploying the unexpanded implant from the sheath.

In an embodiment, the sheath, when deployed from the microcatheter, (a) prevents the unexpanded implant from expanding, and (b) permits the unexpanded implant, located within the sheath, to be retracted back into the microcatheter after having been deployed from the microcatheter.

In an embodiment, the maximum outer diameter of the sheath is located proximal to the distal end portion of the sheath. In such a case, distal portions of the sheath may be allowed past (or distal) the collar. The more proximally located maximum diameter of the sheath may eventually be stopped by the collar, but not until after the distal portion of the sheath has extended past the collar and past the tip of the microcatheter.

In an embodiment the microcatheter and the collar are monolithic with one another (e.g., formed from a single mold). Doing so may help ensure the collar does not separate from the catheter when the implant (e.g., foam) is pushed out from the catheter and into the patient. Also, the collar may include a circular opening from which the unexpanded implant is deployed. However, other shapes are possible (e.g., ovular).

Also, in an embodiment the unexpanded implant is pre-loaded near the distal end portion of the sheath before the sheath is deployed into the microcatheter. This may shorten the distance that the implant may need to be pushed while the sheath is stationary. In other words, if resistance based on the foam is high then deployment of the foam is facilitated by shortening the distance the foam must travel (while pushing against side walls of the sheath) while the sheath is stationary.

In an embodiment, the unexpanded implant comprises a SMP having a glass transition temperature (Tg) less than 100 degrees Fahrenheit. Such an SMP may expand to its primary shape based on body temperature.

An embodiment includes a SMP that covers a majority of the backbone and is greater than 5 cm in length. However, other lengths including 3, 4, 6, 7, 8, 9 cm and the like are included in other embodiments.

In an embodiment a retainer (that stops sheath advancement) may be located proximal to the proximal tip of the microcatheter when the implant advances past the distal tip of the halted sheath and into a patient. Such a retainer may be a collar located proximal to the distal end of a catheter. The retainer may be similar to collar 1325, clamps 1210 and 1211, collar 1525, and the like.

An embodiment includes a sheath that (a) prevents the implant from expanding, and/or (b) permits the implant, while located within the sheath, to be retracted back into the catheter after having been deployed from the catheter.

An embodiment includes a sheath that is configured so, when deployed from the catheter, the sheath permits the already expanded implant to be retracted back into the sheath, compressed within the sheath, and then retracted back into the catheter.

Another embodiment includes a method comprising: providing an expandable implant, a flexible hollow sheath, a flexible hollow catheter, and a retainer coupled to the catheter. A user may insert the catheter, sheath, and implant into a patient and then (a) simultaneously advance the sheath and the implant within the catheter until the sheath is halted by the retainer; and (b) advance the implant past the retainer, out from the sheath, and into the patient. In one embodiment, the simultaneous advancement is fostered by the implant being loaded in the sheath before inserting the sheath into the patient.

An embodiment may allow (after advancing the implant into the patient and expanding the deployed implant) simultaneously retracting the expanded implant and the sheath back into the catheter. The may be facilitated based on the modulus of the expanded implant (i.e., the stiffness of the expanded implant may be such that it can be withdrawn into the sheath and/or catheter). The method may further allow compressing the expanded implant within the sheath based on retracting the sheath back into the catheter.

In one embodiment, the microcatheter may include an inner diameter of approximately 0.483 mm and the SMP may include a volume expansion of 80×. A 10 mm diameter aneurysm may require more than a single piece of foam. As described above, several embodiments including one or more expansion elements are disclosed. One such embodiment includes a SMP foam formed over a wire backbone with a 3D form. Depending on the 3D geometry of the wire backbone, one SMP foam may adequately fill the aneurysm with a single deployment. However, in other embodiments one may apply a "Russian doll" method that requires multiple (e.g., 2, 3, or more) deployments using devices with successively smaller 3D geometries. In addition, in an embodiment one may initially deploy a standard 3D "framing" coil followed by any of the various embodiments described herein. Also, any of the various embodiments described herein may serve as a framing structure followed by deployment of coils (e.g., GDCs).

One embodiment includes a SMP foam on a wire (e.g. Nitinol, platinum) backbone that is delivered into an anatomical void (e.g., aneurysm). For example, a polymer coated (to bond with foam) wire backbone (0.050 mm diameter) with 3D primary form or state (e.g., about 10-20 cm long in straight form). The embodiment may include a SMP foam with 80× volume expansion (e.g., about 9× radial expansion with expanded diameter of about 4.5 mm); expansion at body temperature; cylindrical sections (e.g., each about 1 to 5 mm long) bonded to wire backbone. The sections would provide flexibility in collapsed form. There may be a compressed outer diameter of about 0.33 mm and an expanded diameter of about 2.9 mm. Other embodiments include varying expansion capacities such as, for example, 20×, 40×, 60× (expanded diameter of about 3.9 mm), 100× and the like. Embodiments may include SMPs with varying Tg such as 37, 39, 41, 43 degrees Celsius.

An embodiment may include a microcatheter with a self-centering distal stop. The catheter may have the following dimensions: 2.0F; 0.667 mm outer diameter; 0.483 mm inner diameter. A distal stop (e.g., collar of FIG. 13) halts sheath advancement as foam is pushed out. The distal edge of the collar may be rounded to facilitate retraction of expanded foam back into the sheath prior to detachment of the foam from the deployment system.

An embodiment may include a sheath that confines compressed foam for transport through a microcatheter. This sheath may include a flexible round wire or ribbon (flattened wire) coil, Teflon tube, and the like having dimensions such as, for example, 0.433 mm outer diameter and 0.333 mm inner diameter.

An embodiment may include a pusher to transport sheathed foam through a microcatheter and push compressed foam out of the sheath. A flexible guide wire (i.e., a pusher rod) may be used and may include a ≤0.333 mm diameter (pushable through sheath) having a step transition (e.g., collar or band of FIG. 13) to prevent over pushing. The pusher may also include a mechanism to temporarily anchor the sheath to the pusher until the sheath reaches the distal stop (e.g., grooves on the pusher to accept rounded teeth on the proximal inner surface of the sheath). This may be used if the wire-foam is not attached to the pusher.

An embodiment may use a detachment mechanism (e.g., electrical) at the junction between the pusher and the wire-foam.

An embodiment may use a guide wire that serves as a pusher. The guide wire may be similar to commonly used guide wires. However, in another embodiment one such guide wire may include a floppy distal end, which once removed, may serve as the pusher. The confining sheath may be sized according to the pusher diameter. A detachment mechanism may not be included in all embodiments (i.e., the wire backbone may not be attached to the pusher).

In an embodiment, the foam may be compressed around the wire backbone without being bonded to the backbone. As a result, the foam may not be fixedly coupled to the backbone (e.g., the foam may be able to slide along the backbone) or it may be fixedly coupled to the backbone (e.g., the foam may be unable to slide along the backbone due to, for example, friction between the foam and backbone). In such scenarios the need to coat the wire or synthesize the foam around the wire may be unnecessary. Multiple foam cylinders may be threaded by hand over the bare wire.

Embodiments are not limited to cerebral aneurysms or even aneurysms for that matter. For example, embodiments may be used as implants to fill anatomic voids (e.g., foramen ovale and the like). Embodiments are not limited to SMPs but may use other void filling systems such as other expandable embolizing systems.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An implantable system to fill an anatomic void, the system comprising:
   a carrier element; and
   a shape memory polymer foam covering a majority of the carrier element, the shape memory polymer foam having primary and secondary shapes and including first and second shape memory polymer portions;
   wherein the shape memory polymer foam pivots the first shape memory polymer portion about the second shape memory polymer portion when the shape memory polymer foam is in its primary shape and also when the shape memory polymer foam is in its secondary shape;
   wherein an adhesive couples the shape memory polymer foam to the carrier element with the adhesive adhering to the carrier element and the shape memory polymer foam adhering to the adhesive;
   wherein the adhesive includes an additional polymer.

2. The system of claim 1, wherein the shape memory polymer foam in the secondary shape has a second modulus and in the primary shape has a first modulus, the second modulus being greater than the first modulus.

3. The system of claim 2, wherein the shape memory polymer foam is greater than 5 cm in length.

4. The system of claim 2, wherein:
   the carrier element includes a coil;
   the first and second shape memory polymer portions are severed from one another and no other shape memory polymer portion is between the first and second shape memory polymer portions;
   the coil includes a section located between the first and second shape memory polymer portions.

5. The system of claim 2, wherein the additional polymer includes urethane.

6. The system of claim 5, wherein the additional polymer includes a thermosetting shape memory polymer.

7. The system of claim 5, wherein the shape memory polymer foam is included in a first layer and the additional polymer is included in a second layer.

8. The system of claim 5, wherein the carrier element includes a polymer.

9. The system of claim 8, wherein the carrier element includes a shape memory polymer.

10. The system of claim 2, wherein the carrier element includes a polymer.

11. The system of claim 10, wherein the shape memory polymer foam is radiopaque.

12. The system of claim 10, wherein the shape memory polymer foam has a glass transition temperature less than 37.7 degrees Celsius.

13. The system of claim 10, wherein the first and second shape memory polymer portions are monolithic with each other.

14. An implantable system to fill an anatomic void, the system comprising:
    a carrier element; and
    a shape memory polymer foam on the carrier element, the shape memory polymer foam having primary and secondary shapes and including first and second shape memory polymer portions;
    wherein the shape memory polymer foam pivots the first shape memory polymer portion about the second shape memory polymer portion when the shape memory polymer foam is in its primary shape and also when the shape memory polymer foam is in its secondary shape;
    wherein an adhesive couples the shape memory polymer foam to the carrier element with the adhesive adhering to the carrier element and the shape memory polymer foam adhering to the adhesive, characterized in that the adhesive includes an additional polymer.

15. The system of claim 14, the system comprising:
    an additional shape memory polymer foam on the carrier element, the additional shape memory polymer foam having primary and secondary shapes and including first and second shape memory polymer portions;
    wherein the additional shape memory polymer foam pivots the first shape memory polymer portion of the additional shape memory polymer foam about the second shape memory polymer portion of the additional shape memory polymer foam when the additional shape memory polymer foam is in its primary shape and also when the additional shape memory polymer foam is in its secondary shape;
    wherein the adhesive couples the additional shape memory polymer foam to the carrier element; the additional shape memory polymer foam adhering to the adhesive;
    wherein a space along the carrier element is present between the shape memory polymer foam and the additional shape memory polymer foam.

16. The system of claim 15, wherein the additional polymer includes a thermosetting shape memory polymer.

* * * * *